US011504488B2

(12) United States Patent
Andrus et al.

(10) Patent No.: US 11,504,488 B2
(45) Date of Patent: Nov. 22, 2022

(54) DILUTION SPACER AND METHOD FOR METERED-DOSE INHALER

(71) Applicants: Paul G. Andrus, Ancaster (CA); Gayle R. Campbell-Andrus, Ancaster (CA)

(72) Inventors: Paul G. Andrus, Ancaster (CA); Gayle R. Campbell-Andrus, Ancaster (CA)

(*) Notice: Subject to any disclaimer, the term of this patent is extended or adjusted under 35 U.S.C. 154(b) by 317 days.

(21) Appl. No.: 16/628,972

(22) PCT Filed: Jul. 4, 2018

(86) PCT No.: PCT/CA2018/050814
§ 371 (c)(1),
(2) Date: Jan. 6, 2020

(87) PCT Pub. No.: WO2019/006547
PCT Pub. Date: Jan. 10, 2019

(65) Prior Publication Data
US 2020/0222643 A1     Jul. 16, 2020

Related U.S. Application Data

(63) Continuation-in-part of application No. 15/644,641, filed on Jul. 7, 2017, now Pat. No. 10,052,445.

(51) Int. Cl.
*A61M 15/00* (2006.01)
*B65D 83/54* (2006.01)
*A61M 39/22* (2006.01)

(52) U.S. Cl.
CPC ...... *A61M 15/0086* (2013.01); *A61M 15/009* (2013.01); *A61M 15/0021* (2014.02);
(Continued)

(58) Field of Classification Search
CPC .......... A61M 15/009; A61M 15/0021; A61M 15/0065; A61M 15/0086; A61M 39/22; B65D 83/54
See application file for complete search history.

(56) References Cited

U.S. PATENT DOCUMENTS 4,534,343 A    8/1985   Nowacki et al.
4,852,561 A    8/1989   Sperry
(Continued)

FOREIGN PATENT DOCUMENTS

EP           0 009 667 A1    4/1980
WO    WO 2010/076683 A1    7/2010
WO    WO 2014/143173 A1    9/2014

OTHER PUBLICATIONS

Extended European Search Report for EP Application No. 18827348.6 dated Mar. 5, 2021 in 8 pages.
(Continued)

*Primary Examiner* — Timothy A Stanis
(74) *Attorney, Agent, or Firm* — Knobbe, Martens, Olson & Bear, LLP

(57) ABSTRACT

A dilution spacer for a metered-dose inhaler comprises an enclosure defining a dilution chamber. An ambient air inlet and an outlet are in fluid communication with the dilution chamber. The ambient air inlet is positioned opposite the outlet whereby suction through the outlet from outside the enclosure draws ambient air into the enclosure through the ambient air inlet to generate an airflow path from the ambient air inlet through the dilution chamber and out of the outlet. The dilution spacer may include an actuator inlet configured to securely releasably interengage a metered-dose inhaler actuator mouthpiece, or may include a receptacle having an actuator nozzle and configured to receive a metered-dose inhaler canister, A metered-dose inhaler plume entering the dilution chamber intersects the airflow path thereto and airflow along the airflow path entrains and redirects at least a portion of the metered-dose inhaler plume toward the outlet.

17 Claims, 11 Drawing Sheets

(52) U.S. Cl.
CPC ......... *A61M 15/0065* (2013.01); *B65D 83/54* (2013.01); *A61M 39/22* (2013.01)

(56) References Cited

U.S. PATENT DOCUMENTS

| | | |
|---|---|---|
| 5,012,803 A | 5/1991 | Foley et al. |
| 5,042,467 A | 8/1991 | Foley |
| 6,681,767 B1 | 1/2004 | Patton et al. |
| 7,418,962 B1 | 9/2008 | Rao |
| 8,770,188 B2 | 7/2014 | Stenzler et al. |
| 10,052,445 B1 | 8/2018 | Andrus et al. |
| 2012/0247460 A1 | 10/2012 | Stenzler et al. |
| 2016/0022933 A1 | 1/2016 | Ciancone et al. |
| 2016/0367770 A1 | 12/2016 | Matsuda |

OTHER PUBLICATIONS

International Search Report and Written Opinion in PCT/CA2018/050814 dated Sep. 21, 2018.
International Preliminary Report on Patentability in PCT/CA2018/050814 dated Jan. 7, 2020.

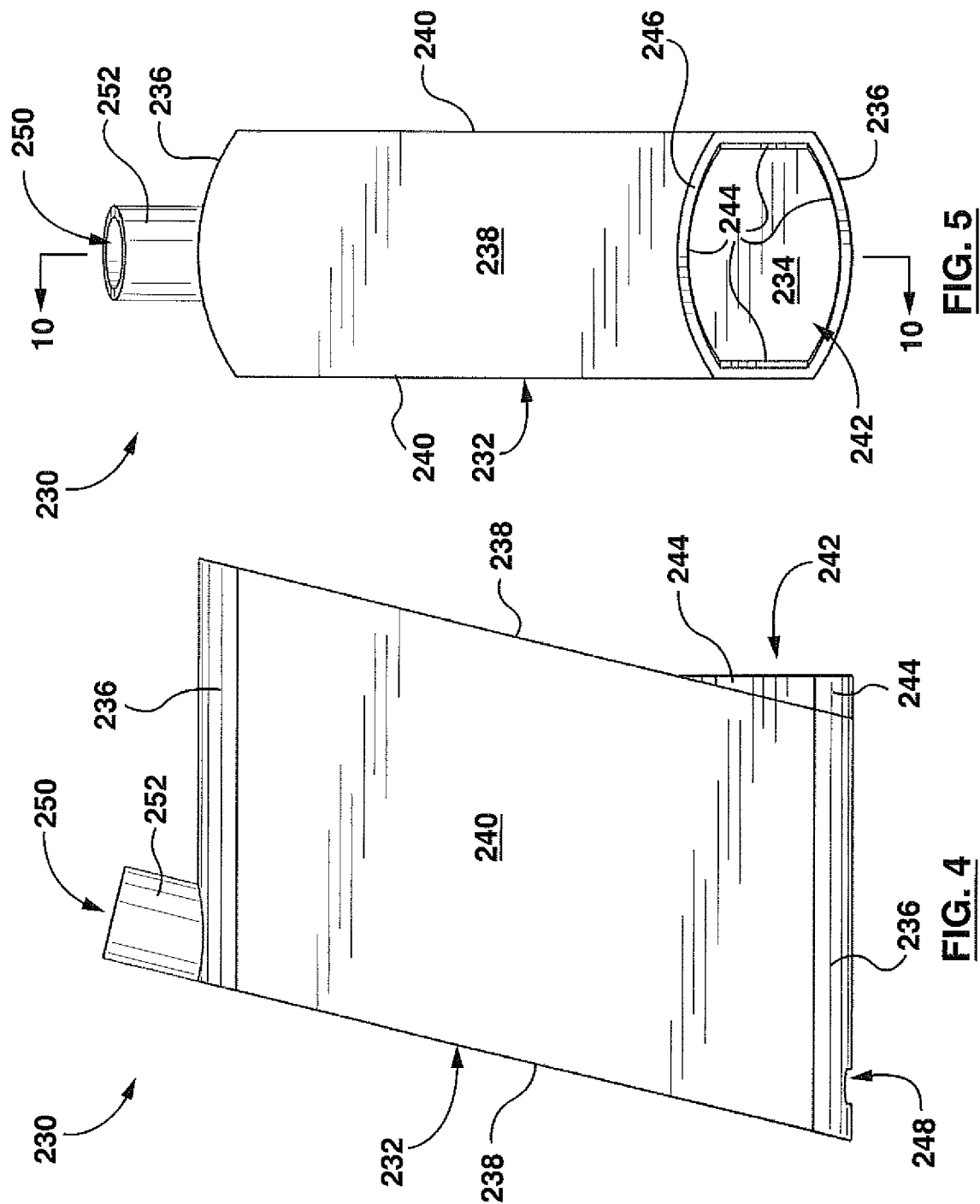

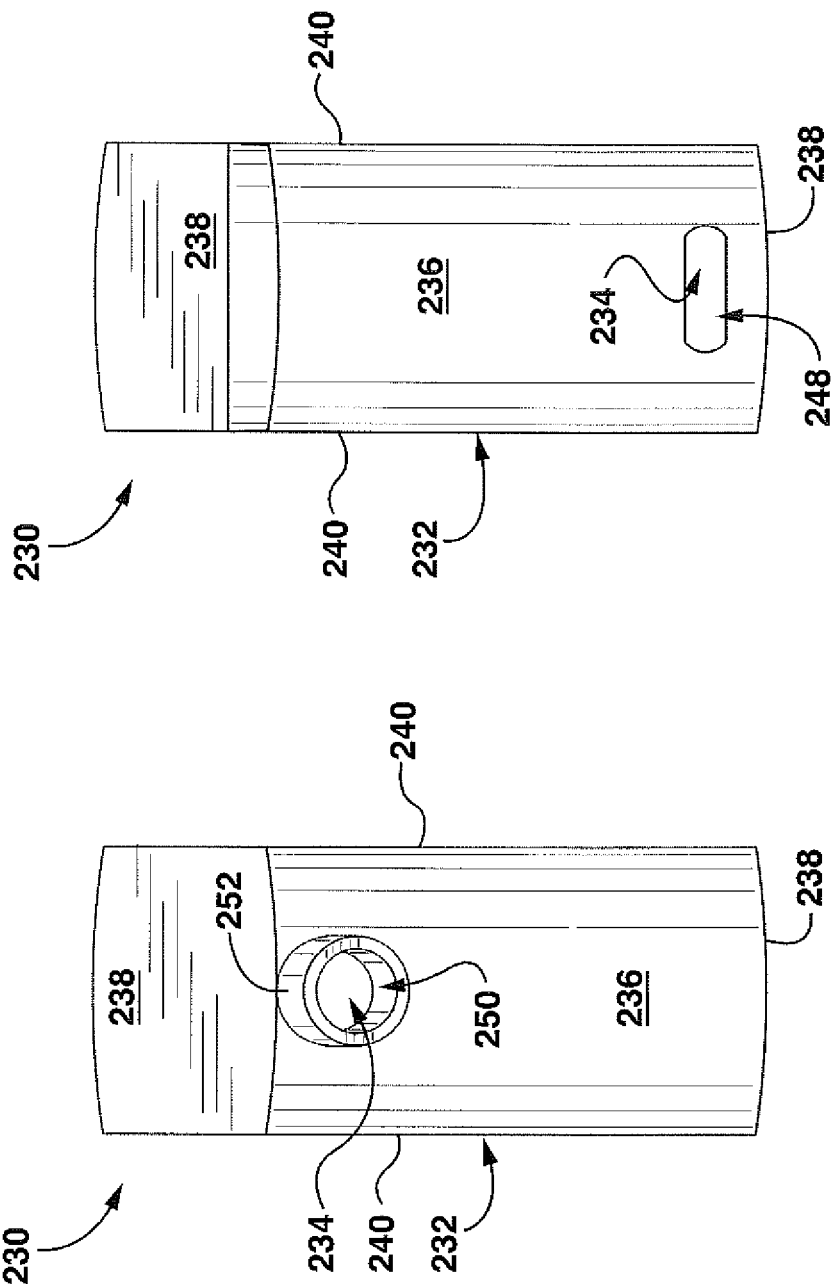

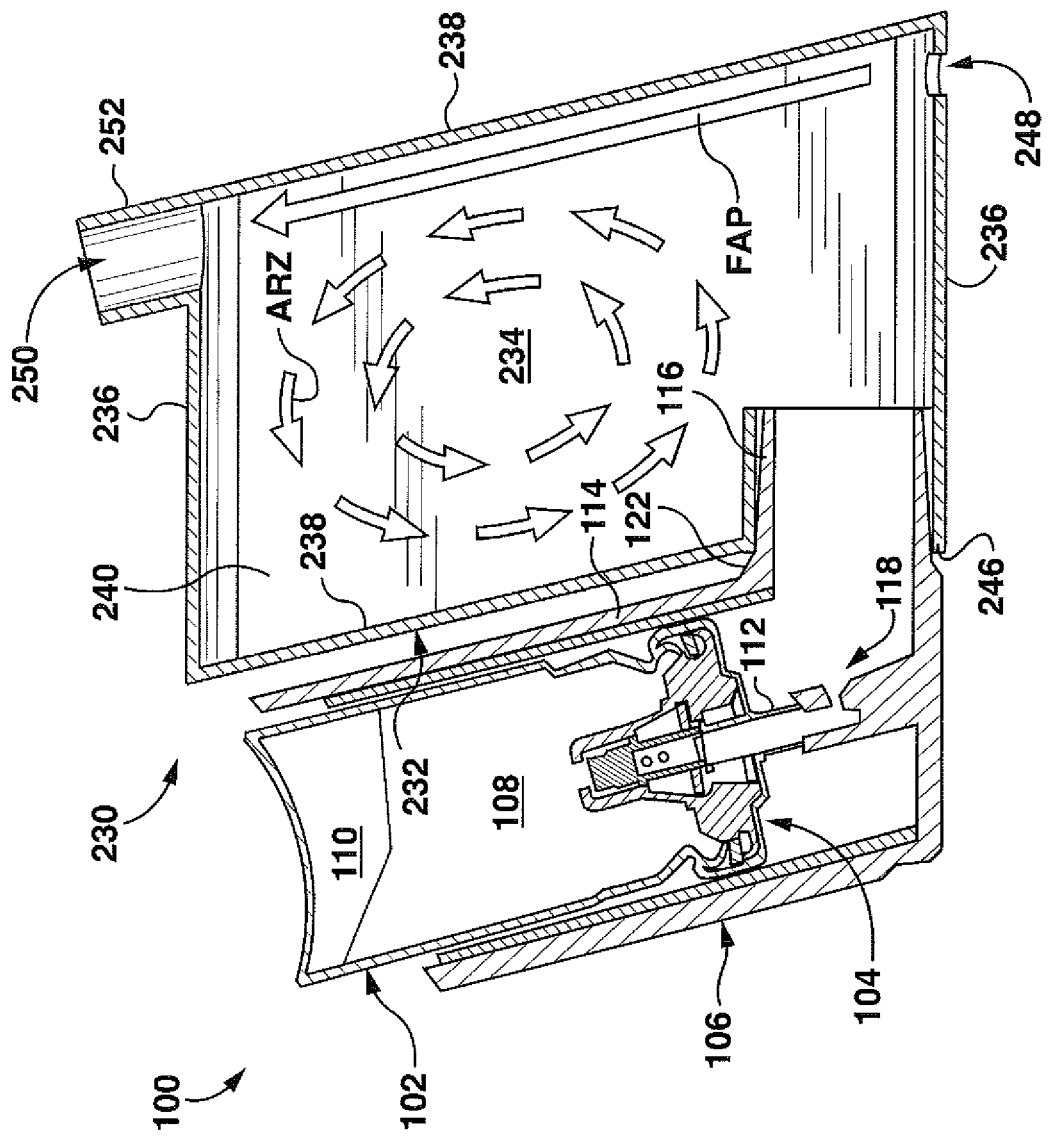

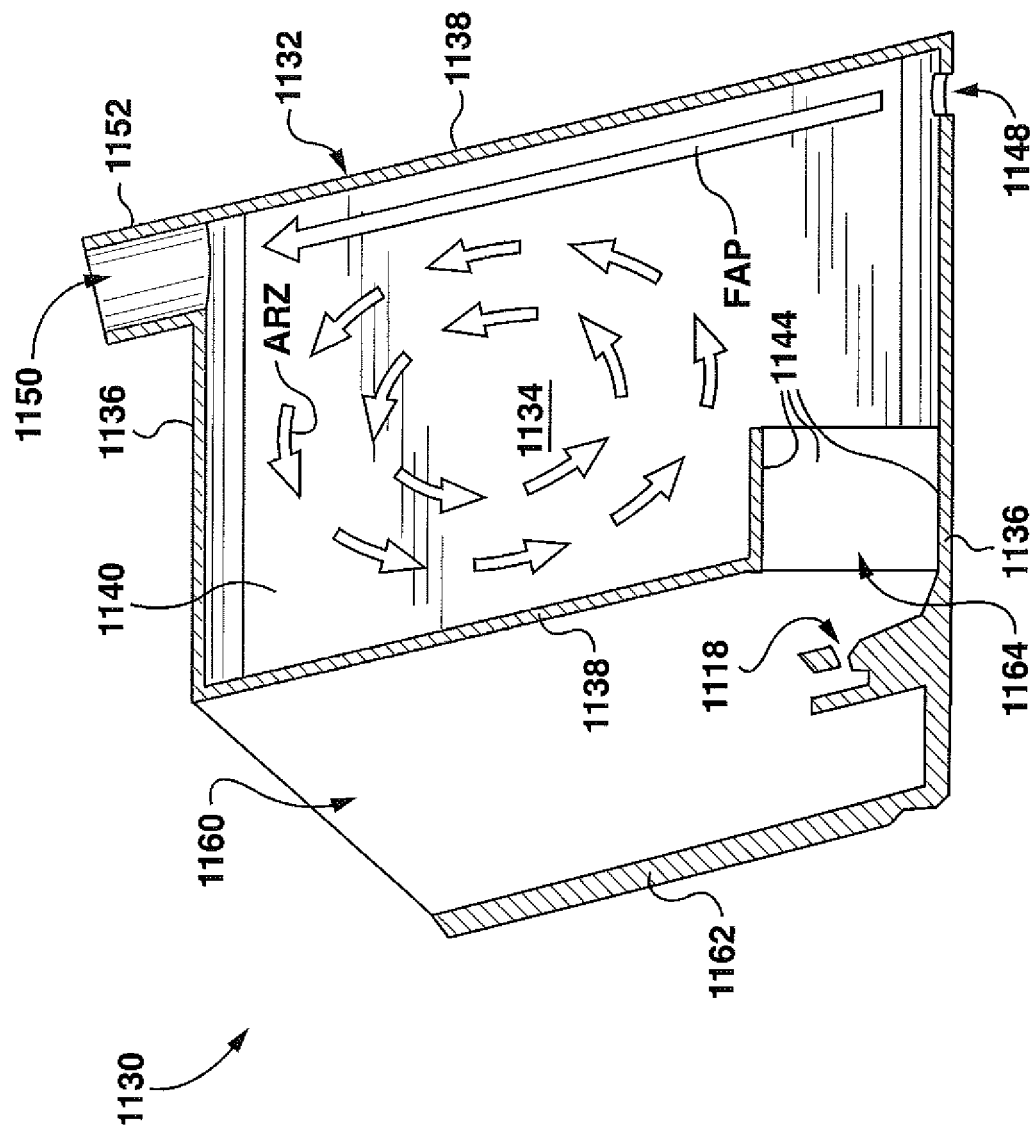

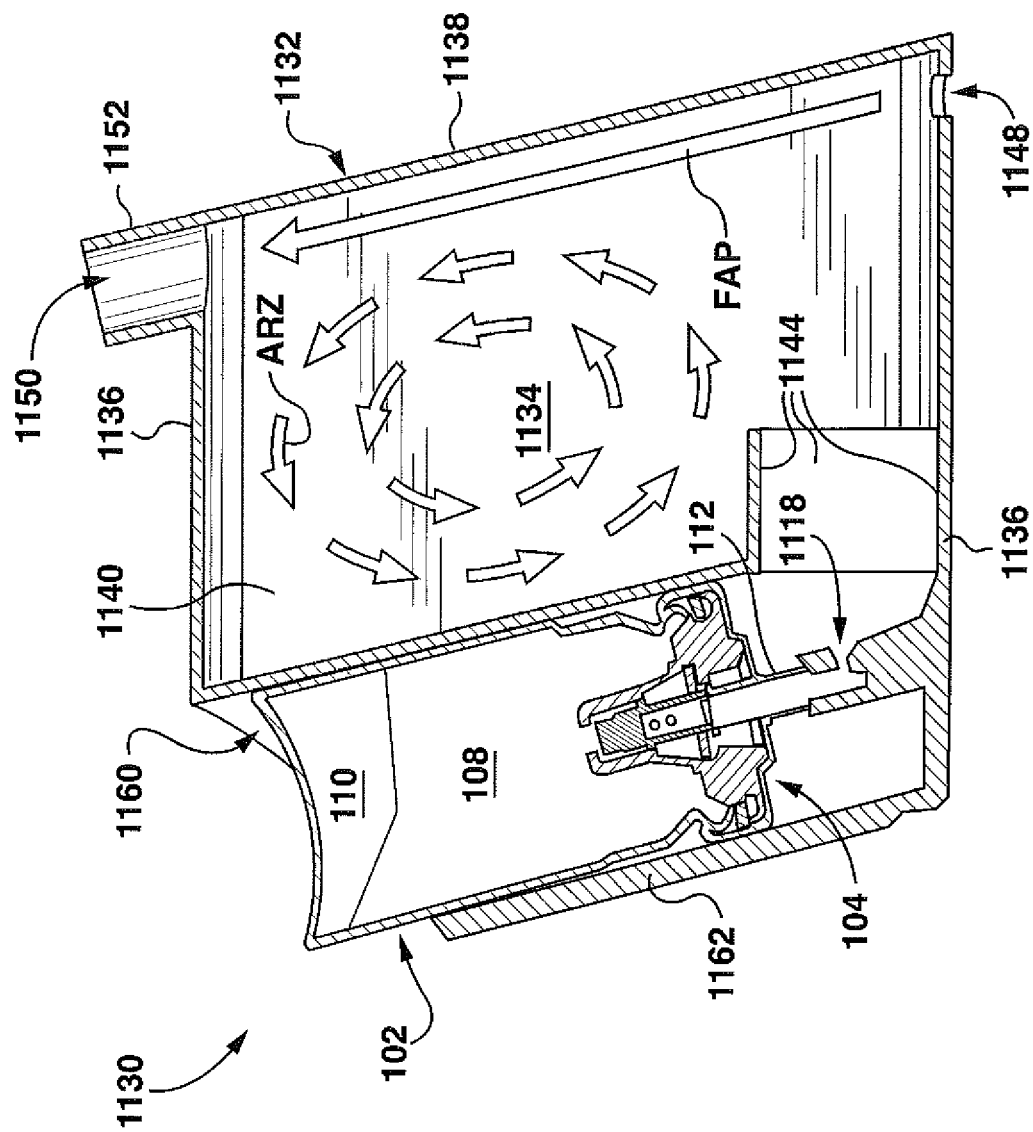

DILUTION SPACER AND METHOD FOR METERED-DOSE INHALER

TECHNICAL FIELD

The present disclosure relates to metered-dose inhalers, and more particularly to dilution spacers for use with metered-dose inhalers.

BACKGROUND

A metered-dose inhaler (MDI) is a device that delivers a measured quantity of aerosolized medication.

Figure 1:
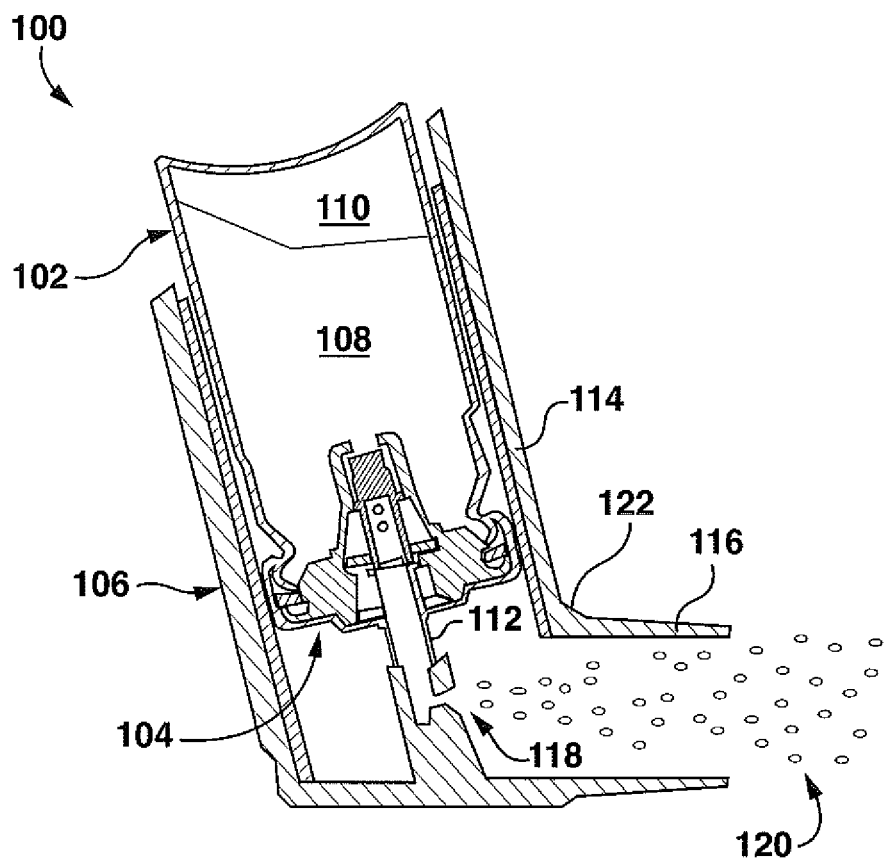
Figure 3:
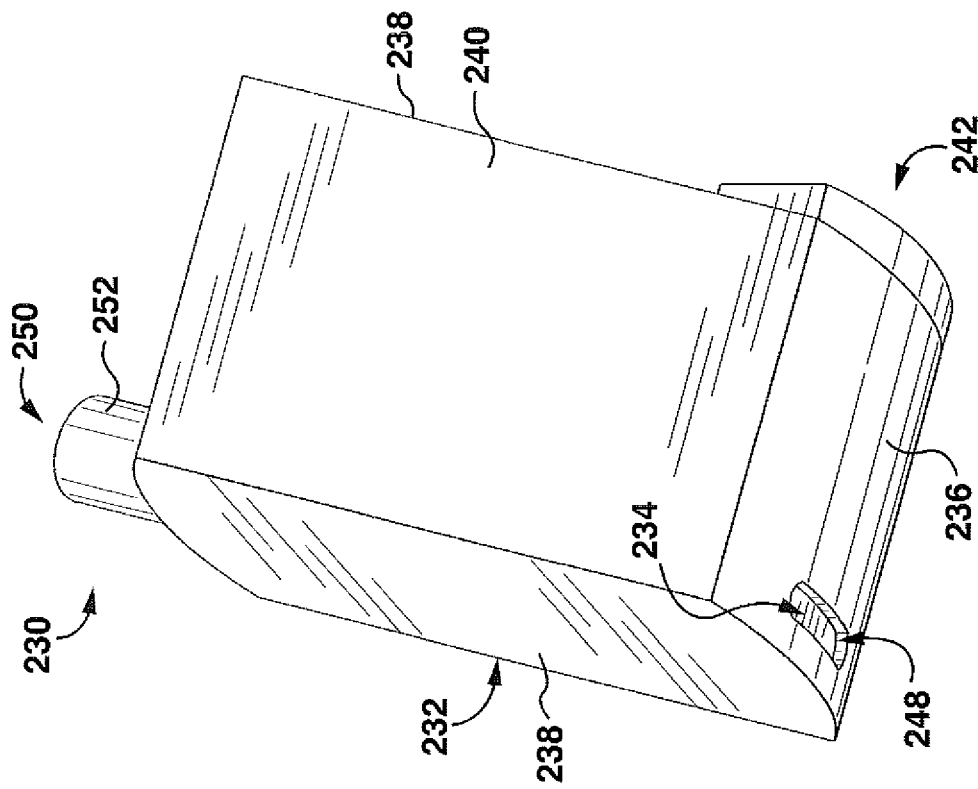
Figure 2:
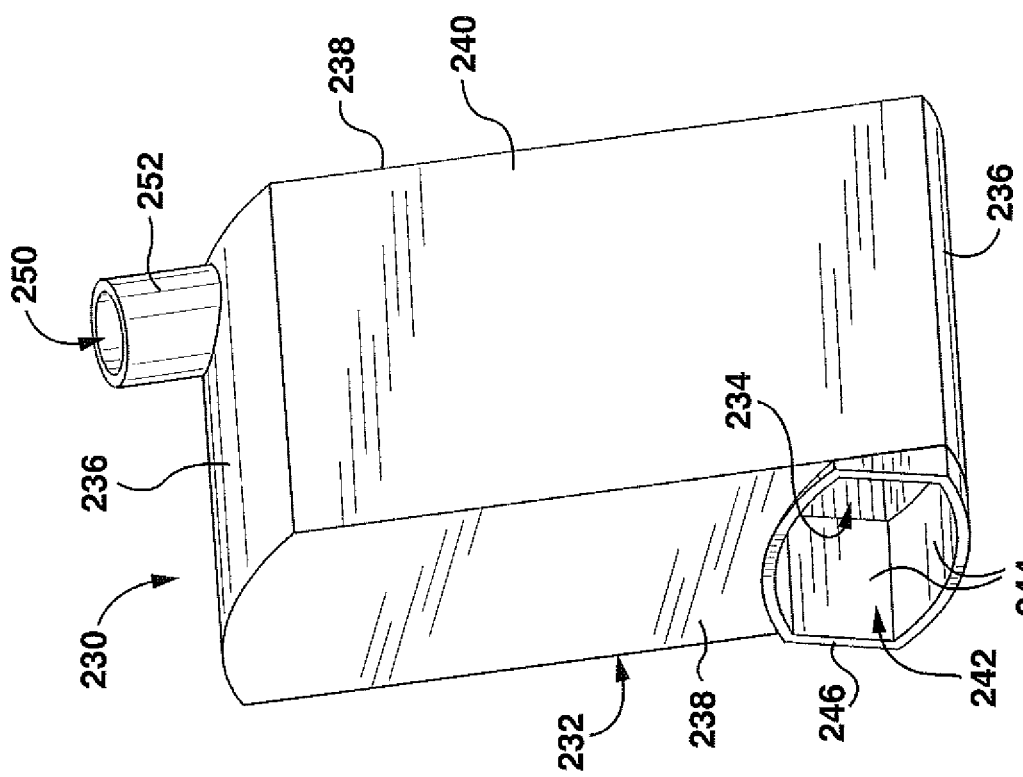
Figure 7:
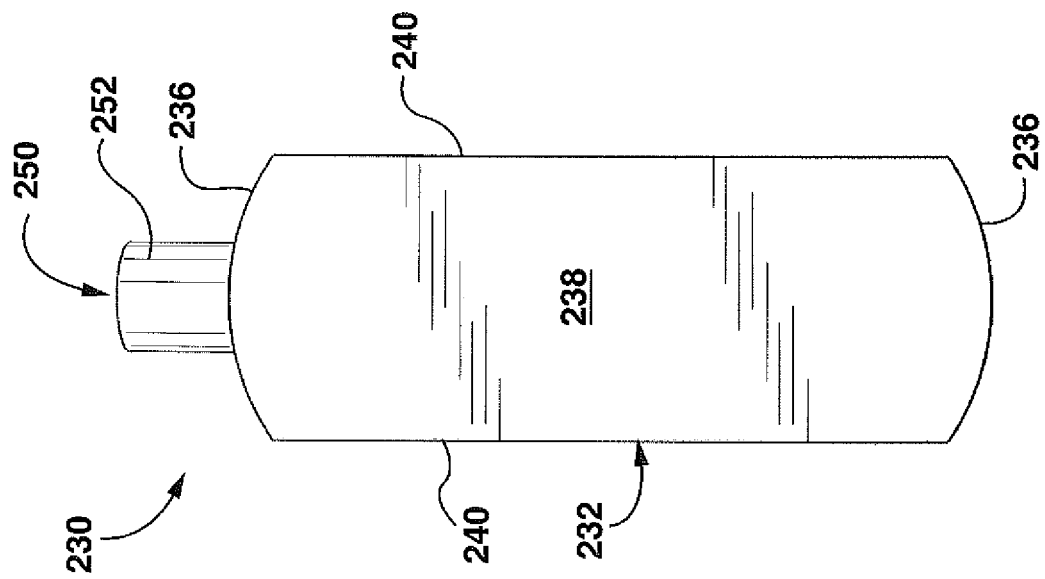
Figure 6:
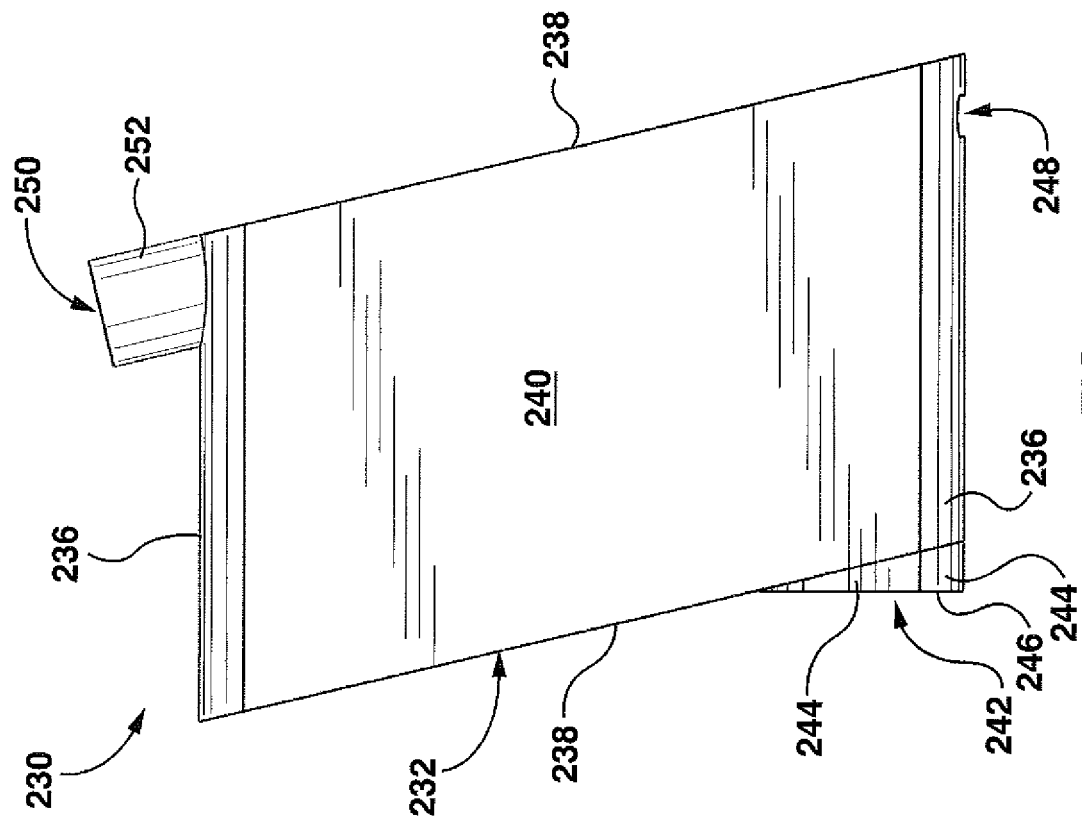

Referring now to FIG. 1, one illustrative example of a metered-dose inhaler, indicated generally by reference 100, will be described. The metered-dose inhaler 100 of FIG. 1 is made up of three primary components: a canister 102, a metering valve 104 and an actuator 106. The canister 102 is typically formed from stainless steel or aluminum, and contains the material to be dispensed; i.e. the medication 108 and propellant 110 (other materials such as excipients may also be included). The metering valve 104 is sealed to the canister 102, and includes a movable hollow valve stem 112. The metering valve 104 is configured so that when the valve stem 112 is moved toward the canister 102 from a containing position into a dispensing position (i.e. when the valve is actuated), a metered quantity of the medication 108 is released from the canister 102 through the valve stem 112. The configuration of the metering valve 104 is such that even if the valve stem 112 is maintained in the dispensing position, only the metered quantity of medication 108 is dispensed. Design and construction of metering valves is well known, and is not discussed further. The actuator 106 comprises a hollow body 114 that receives the canister 102, a mouthpiece 116, typically projecting obliquely from the body 114, and an actuator nozzle 118, also referred to as an atomizing nozzle, projecting inwardly at the junction of the body 114 and the mouthpiece 116. The valve stem 112 is received by the actuator nozzle 118 in fluid communication therewith so that pushing the canister 102 toward the actuator nozzle 118 moves the valve stem 112 (relative to the canister 102) into the dispensing position and releases the metered quantity of medication 108 into the actuator nozzle 118. The actuator nozzle 118 is configured to generate a plume 120 from the contents of the metered-dose inhaler canister 102 received through the valve stem 112 and direct the plume 120 through the mouthpiece 116. A patient would administer a dose of the medication 108 by pressing the canister 102 into the body 114 of the actuator 104 while inhaling through the mouthpiece 106.

Inhaling directly from a metered-dose inhaler can be difficult, and patients may use a tube having a mouthpiece at one end and a receptacle that receives the actuator mouthpiece 116 at the other end. These tubes, referred to as holding chambers or spacers, function as a reservoir to contain the metered dose inhaler plume 120, making it easier to inhale. However, such holding chambers or spacers are generally large and cumbersome.

SUMMARY

In one aspect, a dilution spacer for a metered-dose inhaler comprises an enclosure defining a dilution chamber, an actuator inlet configured to securely releasably interengage a metered-dose inhaler actuator mouthpiece, an ambient air inlet and an outlet. Each of the actuator inlet, the ambient air inlet and the outlet are in fluid communication with the dilution chamber. The ambient air inlet is positioned opposite the outlet whereby suction through the outlet from outside the enclosure draws ambient air into the enclosure through the ambient air inlet to generate an airflow path from the ambient air inlet through the dilution chamber and out of the outlet. The actuator inlet is positioned relative to the ambient air inlet and the outlet so that a metered-dose inhaler plume entering the dilution chamber through the actuator inlet intersects the airflow path thereto, whereby airflow along the airflow path entrains and redirects at least a portion of the metered-dose inhaler plume toward the outlet.

The dilution spacer may be incorporated into an assembly further comprising a metered-dose inhaler actuator whose actuator mouthpiece is securely releasably interengaged in the actuator inlet. The actuator mouthpiece may, for example, be friction fit in the actuator inlet or be interference fit in the actuator inlet.

The assembly may further comprise a metered-dose inhaler canister received in the body of the metered-dose inhaler actuator, and the valve stem of the metering valve sealed to the metered-dose inhaler canister may be received by the actuator nozzle of the metered-dose inhaler actuator. The actuator nozzle is configured to generate a metered-dose inhaler plume from contents of the metered-dose inhaler canister and direct the metered-dose inhaler plume into the dilution chamber through the actuator mouthpiece and the actuator inlet. In certain preferred embodiments, the actuator nozzle is configured to direct the metered-dose inhaler plume at an oblique angle to the valve stem.

In some embodiments, the enclosure is generally parallelepipedic, the actuator mouthpiece of the metered-dose inhaler actuator is at an oblique angle to the body of the metered-dose inhaler actuator and the body of the metered-dose inhaler actuator is substantially flush with an edge of the enclosure in which the actuator inlet is formed.

In certain preferred embodiments, the metered-dose inhaler plume entering the dilution chamber through the actuator inlet intersects the airflow path non-parallel thereto, and in certain particular embodiments, the airflow redirects at least a portion of the metered-dose inhaler plume by about 103.5 degrees.

In some embodiments, the outlet comprises a dilution spacer mouthpiece projecting outwardly from the enclosure.

In another aspect, a metered-dose inhaler actuator comprises an enclosure defining a dilution chamber, a receptacle having an actuator nozzle and configured to receive a metered-dose inhaler canister so that the valve stem of the metering valve sealed to the metered-dose inhaler canister is received by the actuator nozzle, and further comprises an ambient air inlet and an outlet. Each of the actuator nozzle, the ambient air inlet and the outlet are in fluid communication with the dilution chamber. The ambient air inlet is positioned opposite the outlet whereby suction through the outlet from outside the enclosure draws ambient air into the enclosure through the ambient air inlet to generate an airflow path from the ambient air inlet through the dilution chamber and out of the outlet. The actuator nozzle is configured to generate a metered-dose inhaler plume from contents of the metered-dose inhaler canister and direct the metered-dose inhaler plume into the dilution chamber. The actuator nozzle is positioned relative to the ambient air inlet and the outlet so that the metered-dose inhaler plume intersects the airflow path, whereby airflow along the airflow path entrains and redirects at least a portion of the metered-dose inhaler plume toward the outlet.

In some embodiments, the outlet comprises a mouthpiece projecting outwardly from the enclosure.

The metered-dose inhaler actuator may be incorporated into an assembly further comprising a metered-dose inhaler canister received within the receptacle with the valve stem of the metering valve of the metered-dose inhaler canister received by the actuator nozzle. In certain preferred embodiments, the actuator nozzle is configured to direct the metered-dose inhaler plume at an oblique angle to the valve stem.

Figure 10:
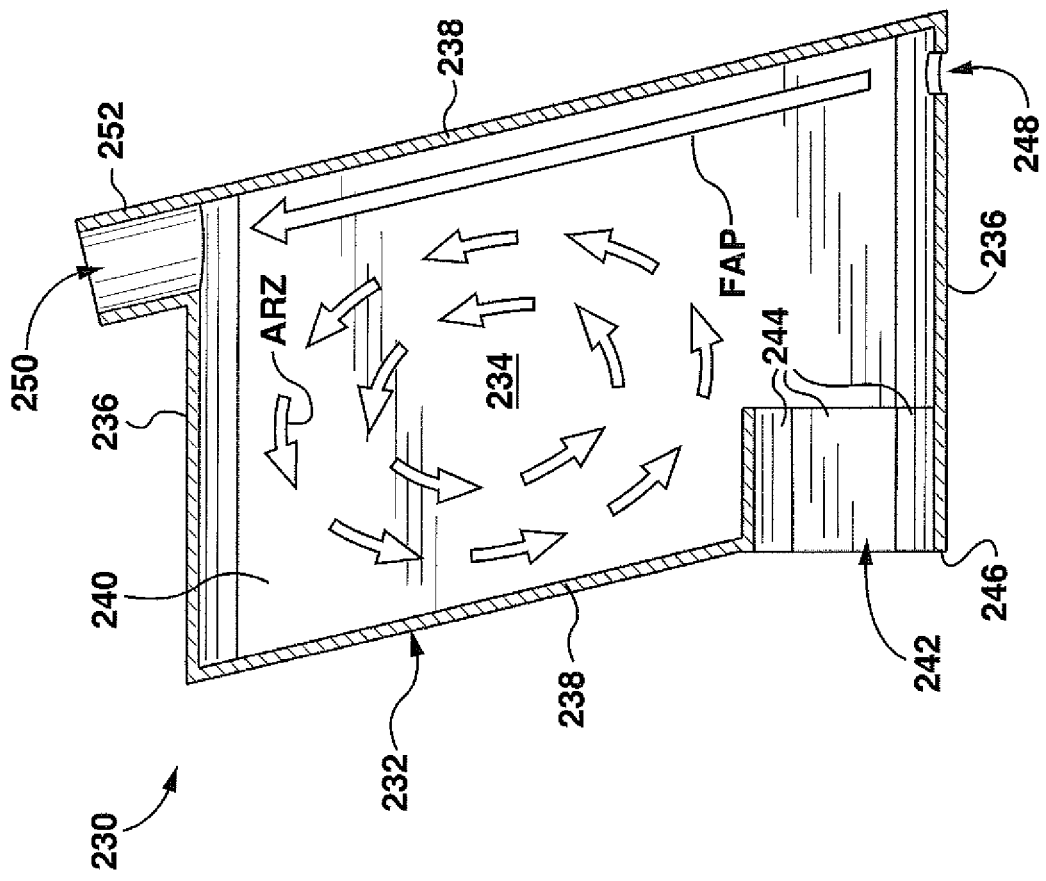
Figure 10B:
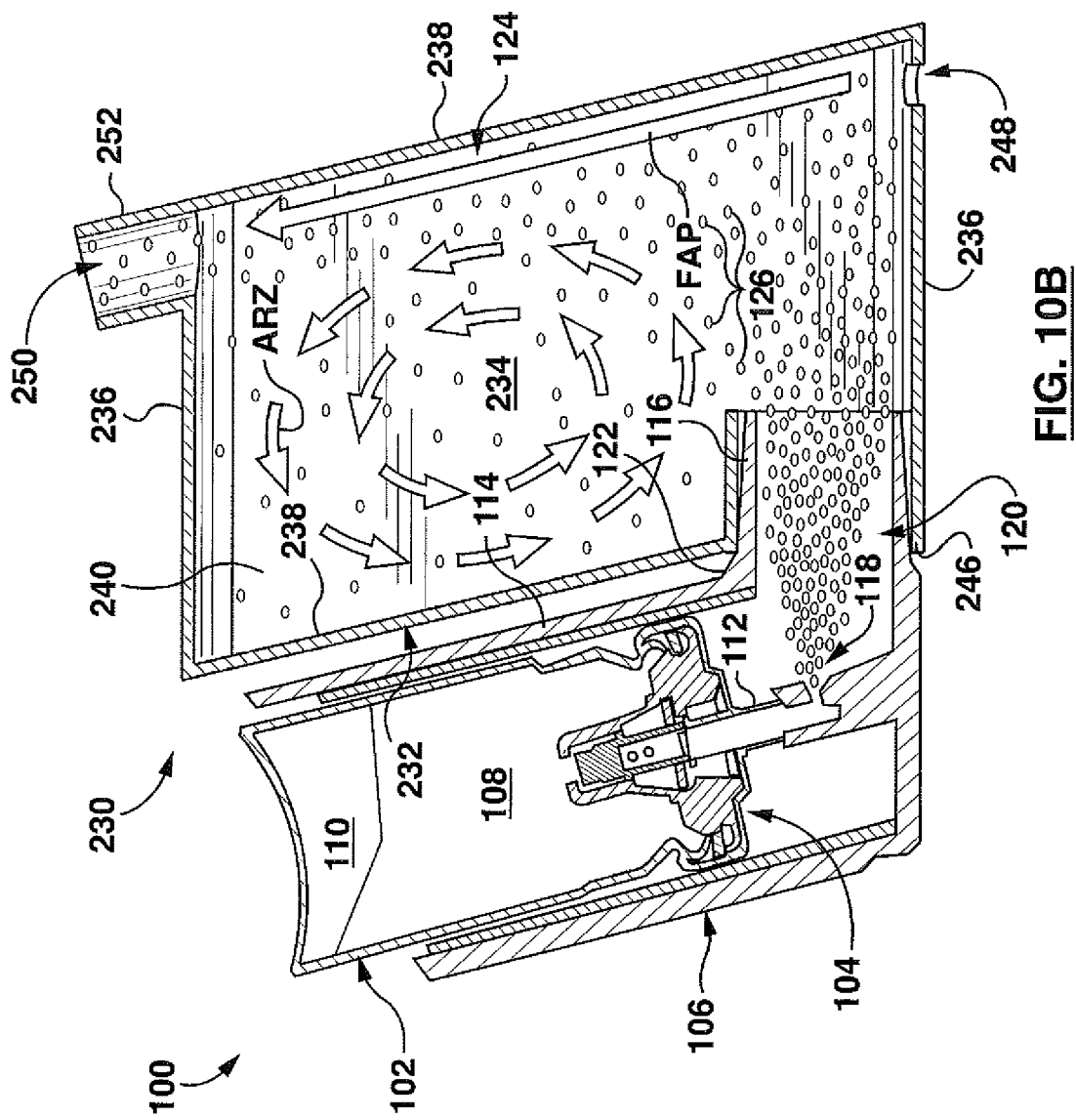

In certain preferred embodiments, the metered-dose inhaler plume entering the dilution chamber through the actuator inlet intersects the airflow path non-parallel thereto, and in certain particular embodiments, the airflow redirects at least a portion of the metered-dose inhaler plume by about 103.5 degrees.

BRIEF DESCRIPTION OF THE DRAWINGS

These and other features will become more apparent from the following description in which reference is made to the appended drawings wherein:

FIG. 1 is a side cross-sectional view of an illustrative metered-dose inhaler;

FIG. 2 is a top front perspective view of an illustrative dilution spacer for a metered-dose inhaler;

FIG. 3 is a bottom rear perspective view of the dilution spacer of FIG. 2;

FIG. 4 is a right side elevation view of the dilution spacer of FIG. 2;

FIG. 5 is a front elevation view of the dilution spacer of FIG. 2;

FIG. 6 is a left side elevation view of the dilution spacer of FIG. 2;

FIG. 7 is a rear elevation view of the dilution spacer of FIG. 2;

FIG. 8 is a top plan view of the dilution spacer of FIG. 2;

FIG. 9 is a bottom plan view of the dilution spacer of FIG. 2;

FIG. 10 is a cross-sectional view of the dilution spacer of FIG. 2, taken along the line 10-10 in FIG. 5;

FIGS. 10A and 10B show cross-sectional views of the dilution spacer of FIG. 2, taken along the line 10-10 in FIG. 5, in combination with the metered-dose inhaler of FIG. 1;

FIG. 11 is a cross-sectional view of an illustrative metered-dose inhaler actuator; and FIGS. 11A and 11B show cross-sectional views of the metered-dose inhaler actuator of FIG. 11 in combination with a metered-dose inhaler canister and metering valve.

DETAILED DESCRIPTION

Reference is now made to FIGS. 2 to 11, with particular emphasis on the cross-sectional views shown in FIGS. 10 to 10B. In FIGS. 2 to 11, an illustrative dilution spacer for a metered-dose inhaler is indicated generally by reference 230. The dilution spacer 230 comprises an enclosure 232 defining a dilution chamber 234 (FIGS. 10 to 10B). In the illustrative embodiment shown in FIGS. 2 to 10B, the enclosure 232 is generally parallelepipedic and is formed by three pairs of opposed walls. More particularly, the enclosure 232 is formed by a pair of opposed outwardly curved end walls 236, a pair of opposed generally planar edge walls 238 and a pair of opposed generally planar side walls 240. Although the end walls 236 are generally curved, the overall shape of the enclosure is generally parallelepipedic. The shape of the enclosure 232 shown in FIGS. 2 to 11 is merely illustrative, and a wide range of shapes may be applied to the enclosure without departing from the scope of the present disclosure.

An actuator inlet 242 is formed through one of the edge walls 238, and is in fluid communication with the dilution chamber 234. The actuator inlet 242 is configured to securely releasably interengage an actuator mouthpiece 116, as shown in FIGS. 10A and 10B, and includes inlet walls 244 (best seen in FIG. 10) whose size and shape is complementary to that of the actuator mouthpiece 116 to be received. In the illustrated embodiment, the actuator inlet 242 includes an alignment lip 246. As can be seen in FIGS. 10A and 10B, the actuator mouthpiece 116 of the actuator 104 is at an oblique angle to the body 114 of the actuator 104 and the alignment lip 246 engages a shoulder 122 on the actuator mouthpiece 116. In the illustrated embodiment, the angle formed between the body 114 of the actuator 104 and the actuator mouthpiece 116 is approximately equal to the angle between the edge wall 238 in which the actuator inlet 242 is formed and the end wall 236 adjacent the actuator inlet 242; the angle will depend on the geometry of the actuator 106 with which the dilution spacer 230 is to be used. As a result, when the actuator mouthpiece 116 is received in the actuator inlet 242, the body 114 of the actuator 104 is substantially flush with the edge wall 238 in which the actuator inlet 242 is formed and therefore is substantially flush with that edge of the enclosure 232; there may be a small gap as shown in the drawings. The actuator mouthpiece 116 may be friction fit in the actuator inlet 242 or interference fit in the actuator inlet, or may be secured by other suitable technique.

An ambient air inlet 248 is formed through one of the end walls 236 and an outlet 250 is formed through the other one of the end walls 236 and positioned opposite the ambient air inlet. In the illustrated embodiment, the outlet 250 comprises a dilution spacer mouthpiece 252 projecting outwardly from the respective end wall 236 and hence outwardly from the enclosure 232; in alternate embodiments the dilution spacer mouthpiece may have a wide range of different shapes or may be omitted and the outlet may consist of a simple aperture through the respective end wall. The ambient air inlet 248 and the outlet 250 are in fluid communication with the dilution chamber 234.

Reference is now made to FIG. 10A, which shows an assembly comprising the dilution spacer 230 in combination with a metered-dose inhaler 100 as shown in FIG. 1. As described above, the metered-dose inhaler 100 comprises a canister 102, a metering valve 104 and an actuator 106, with the canister 102 received in the body 114 of the actuator 106 such that the valve stem 112 of the metering valve 104, which is sealed to the canister 102, is received by the actuator nozzle 118, which is configured to generate a metered-dose inhaler plume 120 (FIG. 10B) from the medication 108 in the canister 102. As described above, the actuator inlet 242 is configured to securely releasably interengage the actuator mouthpiece 116, and the metered-dose inhaler 100 is coupled to the dilution spacer 230 by interengagement of the actuator mouthpiece 116 and the actuator inlet 242, with the body 114 of the actuator 104 substantially flush with the edge of the enclosure 232. In this position, the actuator nozzle 118 will direct the plume 120 into the dilution chamber 234 through the actuator mouthpiece 116 and the actuator inlet 242; as noted above the actuator nozzle 118 will direct the plume 120 (FIG. 10B) at an oblique angle to the valve stem 112.

Operation of the assembly comprising the dilution spacer 230 and metered-dose inhaler 100 will now be described with reference to FIG. 10B. In use, a user would seal his or her mouth around the outlet 250 (e.g. seal his or her lips around the dilution spacer mouthpiece 252) and inhale through his or her mouth. This inhalation creates suction through the outlet 250 from outside the enclosure 232 which, because the ambient air inlet 248 is positioned opposite the outlet 250, draws ambient air into the enclosure 232 through the ambient air inlet 248 to generate a fast airflow path, denoted by arrow FAP, from the ambient air inlet 248 through the dilution chamber 234 and out of the outlet 250 into the user's mouth. The geometry of the dilution chamber 234 formed by the enclosure 232 is such that the inhalation also generates an air recirculation zone, denoted by arrows ARZ, where some of the air drawn into the enclosure 232 bleeds off from the fast airflow path FAP and recirculates.

While inhaling, the user would push the canister 102 toward the actuator nozzle 118 so as to move the valve stem 112 (relative to the canister 102) into the dispensing position and release the metered quantity of medication 108 into the actuator nozzle 118 to generate the plume 120, as shown in FIG. 10B. The actuator inlet 242 is positioned, relative to the ambient air inlet 248 and the outlet 250, so that when the plume 120 enters the dilution chamber 234 through the actuator inlet 242, the plume 120 intersects the fast airflow path FAP. As a result, airflow (generated by the user's inhalation) along the fast airflow path FAP entrains and redirects at least a portion 124 of the plume 120 toward the outlet 250 so that it will be inhaled by the user. The dilution chamber 234 is configured and the actuator inlet 242 is positioned and configured, relative to the ambient air inlet 248 and the outlet 250, so that the plume 120 entering the dilution chamber 234 through the actuator inlet 242 is configured to intersect the fast airflow path FAP. The plume 120 is configured to have adequate distance from the fast airflow path FAP to enable the plume 120 to spread before the plume 120 intersects the fast airflow path FAP and airflow along the fast airflow path FAP is configured to entrain and redirect at least a portion of the plume 120 toward the outlet 250.

The extremely fast aerosol plume 120 from the actuator nozzle 118 has adequate distance to disperse and develop before it then encounters a fast air jet of comparable velocity, namely the airflow along the fast airflow path FAP. This competitive air speed efficiently entrains the aerosol particles 126 that are small enough to penetrate deeply into the lungs, leaving only large particles (which would have ended up in the user's throat with unaided MDI use) to impact the edge wall 238 opposite the actuator nozzle 118. However, because the fast airflow path FAP is narrow and makes up a minority of the volume of the dilution chamber 234, the volumetric flow rate is low. This has the advantage of prolonging and slowing the inhalation cycle and extending the time over which the aerosol particles are delivered. More particularly, because some of the air drawn into the enclosure 232 bleeds off of the fast airflow path FAP and recirculates in the air recirculation zone ARZ with small aerosol particles 126 entrained therein, the effective inhalation cycle is prolonged. As a user continues to inhale after completion of the discharge from the actuator nozzle 118, he or she can continue to inhale dispersed medication as the medicated air from the air recirculation zone ARZ rejoins the fast airflow path FAP. The relative dimensions of the dilution chamber 234 and the position and orientation of the fast airflow path FAP between the ambient air inlet 248 and the outlet 250 facilitates high velocity flow to effectively entrain small aerosol particles 126, but low volumetric flow rate. This is of particular importance for the effective administration of aerosol medication, because it significantly reduces the impact of the timing of MDI actuation relative to the inhalation cycle. As long as MDI actuation occurs after commencement of inhalation and during the early part of a long and slow deep inhalation, the aerosol particles 126 recirculate until depleted or until the user has fully expanded their lungs and cannot further inhale. An additional benefit is that a given dose of aerosol medication is dispersed within a larger volume of inhaled air (as compared to direct inhalation from the MDI or from a conventional holding chamber or spacer), which can increase tolerability of the medication.

Figure 11B:
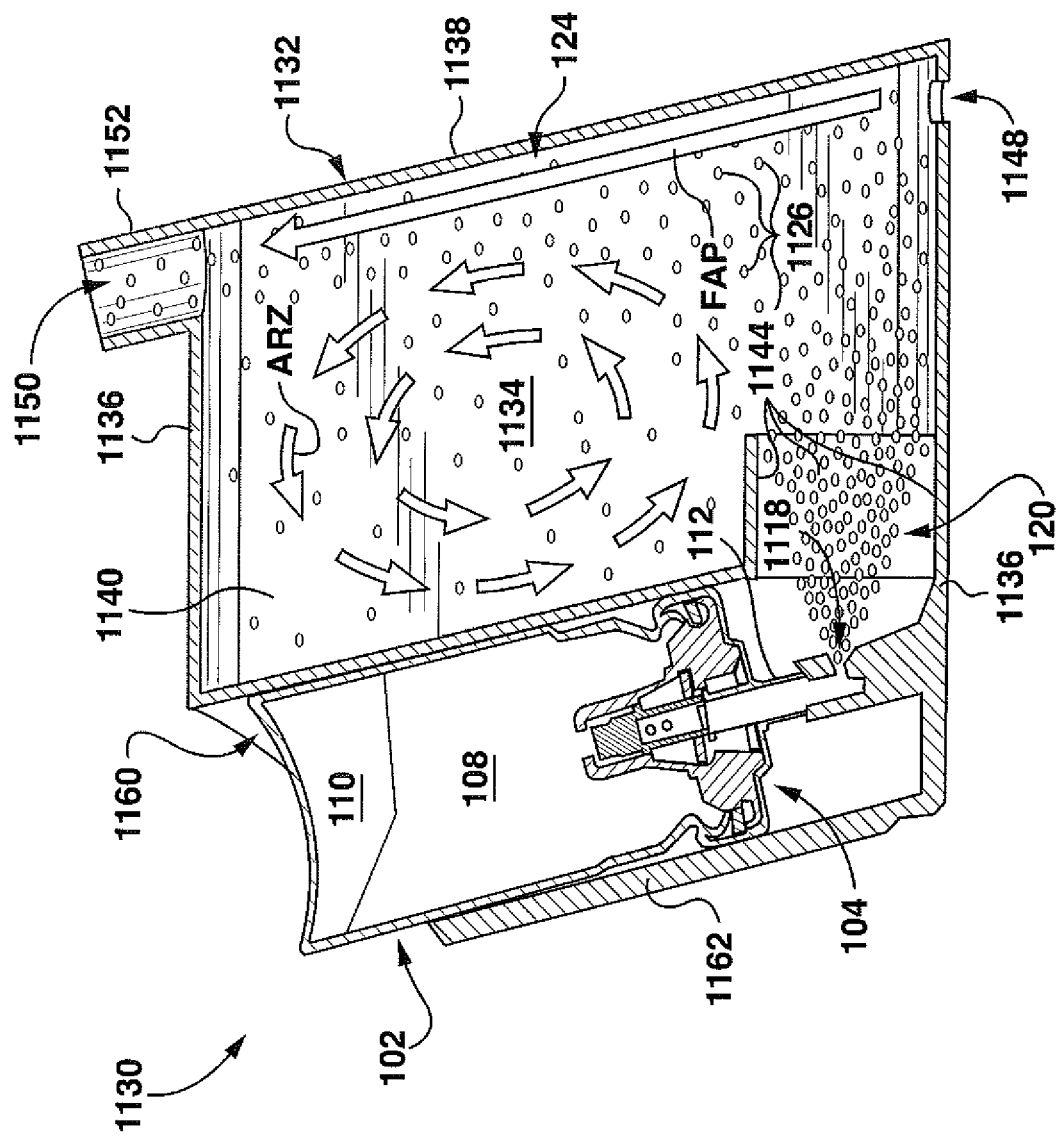

Reference is now made to FIGS. 11 to 11B, in which an illustrative metered-dose inhaler actuator is indicated generally by reference 1130. The metered-dose inhaler actuator 1130 shown in FIGS. 11A and 11B is an apparatus which integrates a metered-dose inhaler actuator and a dilution chamber, and may be considered as a combination of the actuator 106 and the dilution spacer 230 into a single integral unit. As such, like reference numerals denote like features, except with the prefix "11" instead of "2".

The metered-dose inhaler actuator 1130 comprises an enclosure 1132 formed by a pair of opposed outwardly curved end walls 1136, a pair of opposed generally planar edge walls 1138 and a pair of opposed generally planar side walls 1140. While the illustrative enclosure 1132 is generally parallelepipedic, it may have other suitable shapes as well. The enclosure 1132 defines a dilution chamber 1134.

An ambient air inlet 1148 is formed through one of the end walls 1136 and an outlet 1150 is formed through the other one of the end walls 1136 opposite the ambient air inlet. The ambient air inlet 1148 and the outlet 1150 are in fluid communication with the dilution chamber 1134. In the illustrated embodiment, the outlet 1150 comprises an outwardly projecting dilution mouthpiece 1152; in other embodiments the mouthpiece may have different shapes or be omitted entirely.

The metered-dose inhaler actuator 1130 further comprises a receptacle 1160 having an actuator nozzle 1118 and configured to securely releasably receive a metered-dose inhaler canister 102 so that a valve stem 112 of a metering valve 104 sealed to the canister 102 is received by the actuator nozzle 1118, as shown in FIG. 11B. In the illustrated embodiment one of the edge walls 1138 and the end wall 1136 through which the ambient air inlet 1148 is formed cooperates with an encircling wall 1162 to form the receptacle 1160 although other configurations are also contemplated. The actuator nozzle 1118 is in fluid communication with the dilution chamber 1134 through an opening or gap 1164 (FIG. 11) between the edge wall 1138 and the end wall 1136 that form the receptacle 1160 in conjunction with guide walls 1144; in other embodiments the edge wall may extend fully to the end wall and the actuator nozzle may be in fluid communication with the dilution chamber through an aperture in the edge wall.

The actuator nozzle 1118 is configured to generate a plume 120 (FIG. 11B) from the medication 108 in the canister 102 and direct the plume 120 into the dilution chamber 1134 through the gap 1164 between the edge wall 1138 and the end wall 1136; in the illustrated embodiment the actuator nozzle 1118 will direct the plume 120 (FIG. 11B) at an oblique angle to the valve stem 112.

Operation of the metered-dose inhaler actuator 1130 shown in FIGS. 11A and 11B is similar to operation of the assembly comprising the dilution spacer 230 and metered-dose inhaler 100 described with reference to FIGS. 10A and 10B. A user would seal his or her mouth around the outlet 1150 and inhale, creating suction through the outlet 1150 from outside the enclosure 1132. Since the ambient air inlet 1148 is positioned opposite the outlet 1150, this suction draws ambient air into the enclosure 1132 through the ambient air inlet 1148, which generates a fast airflow path FAP from the ambient air inlet 1148 through the dilution chamber 1134 and out of the outlet 1150 into the user's mouth. During inhalation, the user actuates the metering valve 104 to release the metered quantity of medication 108 into the actuator nozzle 1118 to generate the plume 120, as shown in FIG. 11B. The position of the opening or gap 1164 (FIG. 11) relative to the ambient air inlet 1148 and the outlet 1150 is such that when the plume 120 enters the dilution chamber 1134 through the opening or gap 1164 (FIG. 11), the plume 120 intersects the fast airflow path FAP. The inhalation airflow along the fast airflow path FAP then entrains and redirects at least a portion 124 of the plume 120 toward the outlet 1150 to be inhaled by the user. The geometry of the dilution chamber 1134 formed by the enclosure 1132 results in the inhalation generating an air recirculation zone ARZ into which some of the air drawn into the enclosure 1132 bleeds off from the fast airflow path FAP and recirculates. As a user continues to inhale after completion of the discharge from the actuator nozzle 1118, he or she can continue to inhale dispersed medication as the medicated air from the air recirculation zone ARZ rejoins the fast airflow path FAP and moves toward the outlet 1150.

Without being limited by theory, and without promising any particular utility, it is believed that the technology disclosed herein enables a slowing of the ordinarily high inhalation air volumetric flow rate with coincident slowing, dispersion and entrainment of the medication in the plume 120, reducing the timing sensitivity of actuation of the metering valve 104. Instead of having to time inhalation and actuation to be substantially coincident (to achieve inhalation instead of having the medication impact the inside of the mouth or settle inside of a conventional holding chamber or spacer), the user can begin a slow, deep inhalation and then actuate the metering valve 104 while continuing to inhale. Thus, again without being limited by theory, and without promising any particular utility, it is believed that the technology disclosed herein enables a more prolonged inhalation cycle, which facilitates deep lung penetration of the medication while reducing oropharyngeal deposition and dose losses by impaction on the holding chamber or spacer walls, all while maintaining a compact and discreet overall geometry. In the illustrated embodiment, the desired geometry is achieved by turning the aerosol plume 120 by entrainment to flow substantially parallel to the longitudinal axis of the canister 102. Thus, in the illustrated embodiments, the plume 120 entering the dilution chamber 234, 1134 intersects the fast airflow path FAP non-parallel (and also non-perpendicular) thereto and the airflow along the fast airflow path FAP redirects at least a portion of the metered-dose inhaler plume 120 by about 103.5 degrees. In this context, the direction of the plume 120 is defined by a notional centroid line of the plume.

While the illustrated embodiments redirect (at least part of) the plume 120 by about 103.5 degrees, redirection by smaller or larger angles, up to 180 degrees, is also contemplated. In the case of a redirection by 180 degrees (i.e. a reversal of direction), the airflow would surround and move past the canister, but in the opposite direction from that of the plume. In each case, the airflow generated by inhalation is not flowing in the same direction as the plume leaving the actuator nozzle, and in a preferred embodiments the airflow is substantially parallel to the longitudinal axis of the canister.

Certain illustrative embodiments have been described by way of example. It will be apparent to persons skilled in the art that a number of variations and modifications can be made without departing from the scope of the invention as defined in the claims.

What is claimed is:

1. A dilution spacer for a metered-dose inhaler, comprising:
   an enclosure defining a dilution chamber;
   an actuator inlet configured to securely releasably interengage a metered-dose inhaler actuator mouthpiece;
   an ambient air inlet; and
   an outlet;
   wherein:
      each of the actuator inlet, the ambient air inlet and the outlet are in fluid communication with the dilution chamber and the dilution chamber is otherwise sealed;
      the ambient air inlet is positioned opposite the outlet and the ambient air inlet and the outlet are positioned adjacent an edge wall of the enclosure, whereby suction through the outlet from outside the enclosure draws ambient air into the enclosure through the ambient air inlet to generate an airflow path from the ambient air inlet along the edge wall through the dilution chamber and out of the outlet wherein the airflow path makes up a minority of the volume of the dilution chamber; and
      the actuator inlet is positioned relative to the ambient air inlet and the outlet and the dilution spacer is configured so that, in use:
         a metered-dose inhaler plume entering the dilution chamber through the actuator inlet intersects the airflow path; and
         airflow along the airflow path entrains and redirects at least a portion of the metered-dose inhaler plume toward the outlet.

2. An assembly comprising:
   the dilution spacer of claim 1; and
   a metered-dose inhaler actuator whose actuator mouthpiece is securely releasably interengaged in the actuator inlet.

3. The assembly of claim 2, wherein the actuator mouthpiece is friction fit in the actuator inlet.

4. The assembly of claim 2, wherein the actuator mouthpiece is interference fit in the actuator inlet.

5. The assembly of claim 2, wherein:
   a metered-dose inhaler canister is received in a body of the metered-dose inhaler actuator;
   a valve stem of a metering valve sealed to the metered-dose inhaler canister is received by an actuator nozzle of the metered-dose inhaler actuator; and
   the actuator nozzle is configured to:
      generate a metered-dose inhaler plume from contents of the metered-dose inhaler canister; and
      direct the metered-dose inhaler plume into the dilution chamber through the actuator mouthpiece and the actuator inlet.

6. The assembly of claim 5, wherein the actuator nozzle is configured to direct the metered-dose inhaler plume at an oblique angle to the valve stem.

7. The assembly of claim 6, wherein:
   the enclosure is generally parallelepipedic;

the actuator mouthpiece of the metered-dose inhaler actuator is at an oblique angle to the body of the metered-dose inhaler actuator; and the body of the metered-dose inhaler actuator is substantially flush with an edge of the enclosure in which the actuator inlet is formed.

8. The assembly of claim 5, wherein the dilution spacer is configured such that, in use, the metered-dose inhaler plume entering the dilution chamber through the actuator inlet intersects the airflow path non-parallel thereto.

9. The dilution spacer of claim 1, wherein the dilution spacer is configured such that, in use, the airflow redirects at least a portion of the metered-dose inhaler plume by 103.5 degrees.

10. The dilution spacer of claim 1, wherein the enclosure is generally parallelepipedic.

11. The dilution spacer of claim 1, wherein the outlet comprises a dilution spacer mouthpiece projecting outwardly from the enclosure.

12. A metered-dose inhaler actuator, comprising:
an enclosure defining a dilution chamber;
a receptacle having an actuator nozzle and configured to receive a metered-dose inhaler canister so that a valve stem of a metering valve sealed to the metered-dose inhaler canister is received by the actuator nozzle;
an ambient air inlet; and
an outlet;
wherein:
  each of the actuator nozzle, the ambient air inlet and the outlet are in fluid communication with the dilution chamber and the dilution chamber is otherwise sealed;
  the ambient air inlet is positioned opposite the outlet and the ambient air inlet and the outlet are positioned adjacent an edge wall of the enclosure, whereby suction through the outlet from outside the enclosure draws ambient air into the enclosure through the ambient air inlet to generate an airflow path from the ambient air inlet along the edge wall through the dilution chamber and out of the outlet, wherein the airflow path makes up a minority of the volume of the dilution chamber; and
  the actuator nozzle is configured to:
    generate a metered-dose inhaler plume from contents of the metered-dose inhaler canister; and
    direct the metered-dose inhaler plume into the dilution chamber; and
  the actuator nozzle is positioned relative to the ambient air inlet and the outlet and the metered dose inhaler actuator is configured so that, in use:
    the metered-dose inhaler plume intersects the airflow path; and
    airflow along the airflow path entrains and redirects at least a portion of the metered-dose inhaler plume toward the outlet.

13. The metered-dose inhaler actuator of claim 12, wherein the outlet comprises a mouthpiece projecting outwardly from the enclosure.

14. An assembly comprising:
the metered-dose inhaler actuator of claim 12; and
a metered-dose inhaler canister received within the receptacle with the valve stem of the metering valve of the metered-dose inhaler canister received by the actuator nozzle.

15. The assembly of claim 14, wherein the actuator nozzle is configured to direct the metered-dose inhaler plume at an oblique angle to the valve stem.

16. The assembly of claim 14, wherein the metered dose inhaler actuator is configured such that, in use, the metered-dose inhaler plume entering the dilution chamber through the actuator nozzle intersects the airflow path non-parallel thereto.

17. The metered-dose inhaler actuator of claim 12, wherein the metered dose inhaler actuator is configured such that, in use, the airflow redirects at least a portion of the metered-dose inhaler plume by 103.5 degrees.

\* \* \* \* \*